(12) United States Patent
Kawagishi (10) Patent No.: US 11,270,216 B2
(45) Date of Patent: Mar. 8, 2022

(54) DIAGNOSIS SUPPORT APPARATUS, CONTROL METHOD FOR DIAGNOSIS SUPPORT APPARATUS, AND COMPUTER-READABLE STORAGE MEDIUM

(71) Applicant: CANON KABUSHIKI KAISHA, Tokyo (JP)

(72) Inventor: Masami Kawagishi, Kawasaki (JP)

(73) Assignee: Canon Kabushiki Kaisha, Tokyo (JP)

( * ) Notice: Subject to any disclaimer, the term of this patent is extended or adjusted under 35 U.S.C. 154(b) by 818 days.

(21) Appl. No.: 16/079,639

(22) PCT Filed: Feb. 20, 2017

(86) PCT No.: PCT/JP2017/006032
§ 371 (c)(1),
(2) Date: Aug. 24, 2018

(87) PCT Pub. No.: WO2017/150230
PCT Pub. Date: Sep. 8, 2017

(65) Prior Publication Data
US 2019/0042959 A1     Feb. 7, 2019

(30) Foreign Application Priority Data

Mar. 1, 2016  (JP) .............................. JP2016-039197

(51) Int. Cl.
*G06N 5/04*    (2006.01)
*G16H 50/20*    (2018.01)
(Continued)

(52) U.S. Cl.
CPC ............. *G06N 5/046* (2013.01); *G06N 5/045* (2013.01); *G06N 7/005* (2013.01); *G06N 20/00* (2019.01); *G16H 50/20* (2018.01); *G06N 20/10* (2019.01)

(58) Field of Classification Search
CPC ........ G06N 7/005; G06N 20/00; G06N 5/045; G06N 5/046; G06N 20/10; G16H 50/20
See application file for complete search history.

(56) References Cited

U.S. PATENT DOCUMENTS

| 4,649,515 A * | 3/1987 | Thompson ..... G01R 31/318371 706/52 |
| 9,361,580 B2 * | 6/2016 | Kawagishi ............. G06N 7/005 |

(Continued)

FOREIGN PATENT DOCUMENTS

| EP | 2506173 A | 10/2012 |
| EP | 2755154 A | 7/2014 |

(Continued)

OTHER PUBLICATIONS

Written Opinion and International Search Report issued in parent International Application No. PCT/JP2017/006032 dated Jun. 21, 2017.

*Primary Examiner* — Abdullahi E Salad
(74) *Attorney, Agent, or Firm* — Venable LLP (57) ABSTRACT

A diagnosis support apparatus comprising: first inference means for performing inference concerning diagnosis using data collected under a first condition; second inference means for performing inference concerning the diagnosis using the data collected under the first condition and data collected under a second condition different from the first condition; third inference means for performing inference concerning the diagnosis using the data collected under the second condition; and integration means for integrating inference results of the first inference means, the second inference means, and the third inference means using a first weight, a second weight, and a third weight respectively corresponding to the first inference means, the second inference means, and the third inference means.

18 Claims, 8 Drawing Sheets

(51) Int. Cl.
   *G06N 7/00*     (2006.01)
   *G06N 20/00*    (2019.01)
   *G06N 20/10*     (2019.01)

(56)             References Cited

U.S. PATENT DOCUMENTS

| | | | |
|---|---|---|---|
| 9,715,657 B2* | 7/2017 | Kawagishi | G06N 5/04 |
| 10,282,671 B2* | 5/2019 | Kawagishi | G06N 5/02 |
| 2003/0038954 A1* | 2/2003 | Odagiri | H04N 1/6033 |
| | | | 358/1.9 |
| 2011/0246410 A1* | 10/2011 | Iizuka | G06N 20/00 |
| | | | 706/52 |
| 2013/0158398 A1* | 6/2013 | Park | G06T 7/0012 |
| | | | 600/437 |
| 2015/0006447 A1* | 1/2015 | Kawagishi | A61B 6/461 |
| | | | 706/12 |

FOREIGN PATENT DOCUMENTS

| | | |
|---|---|---|
| JP | 2010529529 T | 8/2010 |
| JP | 2014135066 A | 7/2014 |
| WO | 2008148343 A1 | 11/2008 |

\* cited by examiner

DIAGNOSIS SUPPORT APPARATUS, CONTROL METHOD FOR DIAGNOSIS SUPPORT APPARATUS, AND COMPUTER-READABLE STORAGE MEDIUM

TECHNICAL FIELD

The present invention relates to a diagnosis support apparatus, a control method for the diagnosis support apparatus, and a computer-readable storage medium.

BACKGROUND ART

In the medical field, doctors perform the image diagnosis of performing diagnosis by interpreting medical images obtained by imaging apparatuses such as an X-ray CT apparatus and an MRI apparatus. When performing image diagnosis, in accordance with a radiogram interpretation request from a primary doctor, a doctor identifies the symptom of a lesion depicted in an image by comprehensively determining the findings (to be referred to as image findings hereinafter) obtained from the image and information (to be referred to as clinical information hereinafter) about various measurement values and cases. The doctor then compiles the process of reaching the diagnosis into a radiogram interpretation report to the primary doctor as the request source by using the image findings and clinical information. The medical image, image findings, clinical information, and the like will be collectively referred to as medical information hereinafter.

There has been developed a diagnosis support apparatus for supporting such image diagnosis. The diagnosis support apparatus has popularly presented information (to be referred to as support information hereinafter) for supporting diagnosis based on the output of an inference unit using a machine learning technique. In general, an inference unit is formed based on training data (to be referred to as learning data hereinafter) formed by a set of medical information and a correct answer (that is, support information). Then, a correct answer is inferred from medical information (to be referred to as additional data hereinafter) obtained at the time of the operation of the diagnosis support apparatus, and presented as support information. In this case, the apparatus is used on the assumption that the data distribution of pieces of medical information and correct answers and the relationship between medical information and a correct answer exhibit the same tendencies in the learning data and additional data. However, if the collection conditions are different between the learning data and additional data or depending on a lapse of time, data of different tendencies may be obtained. In this state, it is difficult to perform correct inference, and to present appropriate diagnosis support information.

To cope with this problem, Japanese Patent Laid-Open No. 2010-529529 discloses a technique of updating an inference unit using data with which erroneous inference is performed in additional data. In addition, Japanese Patent Laid-Open No. 2014-135066 discloses a technique of creating an inference unit for each of learning data collected in a plurality of facilities, integrating the results of the plurality of inference units in accordance with user settings, and presenting the thus obtained data as support information.

In the technique described in Japanese Patent Laid-Open No. 2010-529529, however, the inference unit is sequentially updated. Thus, if newly collected data exhibits a different tendency at different time, an inference result is unstable, and the inference unit may be updated all the time. In the technique described in Japanese Patent Laid-Open No. 2014-135066, the user needs to set a method of integrating the results of the inference units, thereby imposing a load on the user. Furthermore, since the user can set a method of integrating the results of the respective inference units, support information changes depending on the user settings. That is, an arbitrary operation by the user is unwantedly allowed.

As described above, the conventional techniques have a problem that when a diagnosis support apparatus in which learning data are formed under a given condition (for example, a given facility) is operated under another condition (another facility), it is difficult to smoothly operate the diagnosis support apparatus.

The present invention has been made in consideration of the above problem, and provides a technique in which when a diagnosis support apparatus formed under a given condition is operated under another condition, the diagnosis support apparatus is smoothly operated.

SUMMARY OF INVENTION

According to one aspect of the present invention, there is provided a diagnosis support apparatus comprising: first inference means for performing inference concerning diagnosis using data collected under a first condition; second inference means for performing inference concerning the diagnosis using the data collected under the first condition and data collected under a second condition different from the first condition; third inference means for performing inference concerning the diagnosis using the data collected under the second condition; and integration means for integrating inference results of the first inference means, the second inference means, and the third inference means using a first weight, a second weight, and a third weight respectively corresponding to the first inference means, the second inference means, and the third inference means.

Further features of the present invention will become apparent from the following description of exemplary embodiments with reference to the attached drawings.

DESCRIPTION OF EMBODIMENTS

An exemplary embodiment(s) of the present invention will now be described in detail with reference to the drawings. It should be noted that the relative arrangement of the components, the numerical expressions and numerical values set forth in these embodiments do not limit the scope of the present invention unless it is specifically stated otherwise.

First Embodiment

A diagnosis support apparatus according to the first embodiment obtains medical information (a medical image, image findings, clinical information, and the like) concerning a case as a diagnosis target, and presents information (support information) as a clue for diagnosis on the medical image, thereby performing diagnosis support concerning the case.

In the following description, assume that medical information concerning an abnormal shadow in a lung is obtained as learning data and additional data using the diagnosis support apparatus. Assume also that the abnormality type (diagnosis name) of the abnormal shadow is obtained as a correct answer, and a diagnosis name is inferred using inference units. The inferred result is then presented as support information. A target is not limited to this, and medical information, diagnoses, and the like which will be described below are merely examples for explaining the steps of the processing of the diagnosis support apparatus.

<Arrangement of Diagnosis Support Apparatus>

Figure 1:
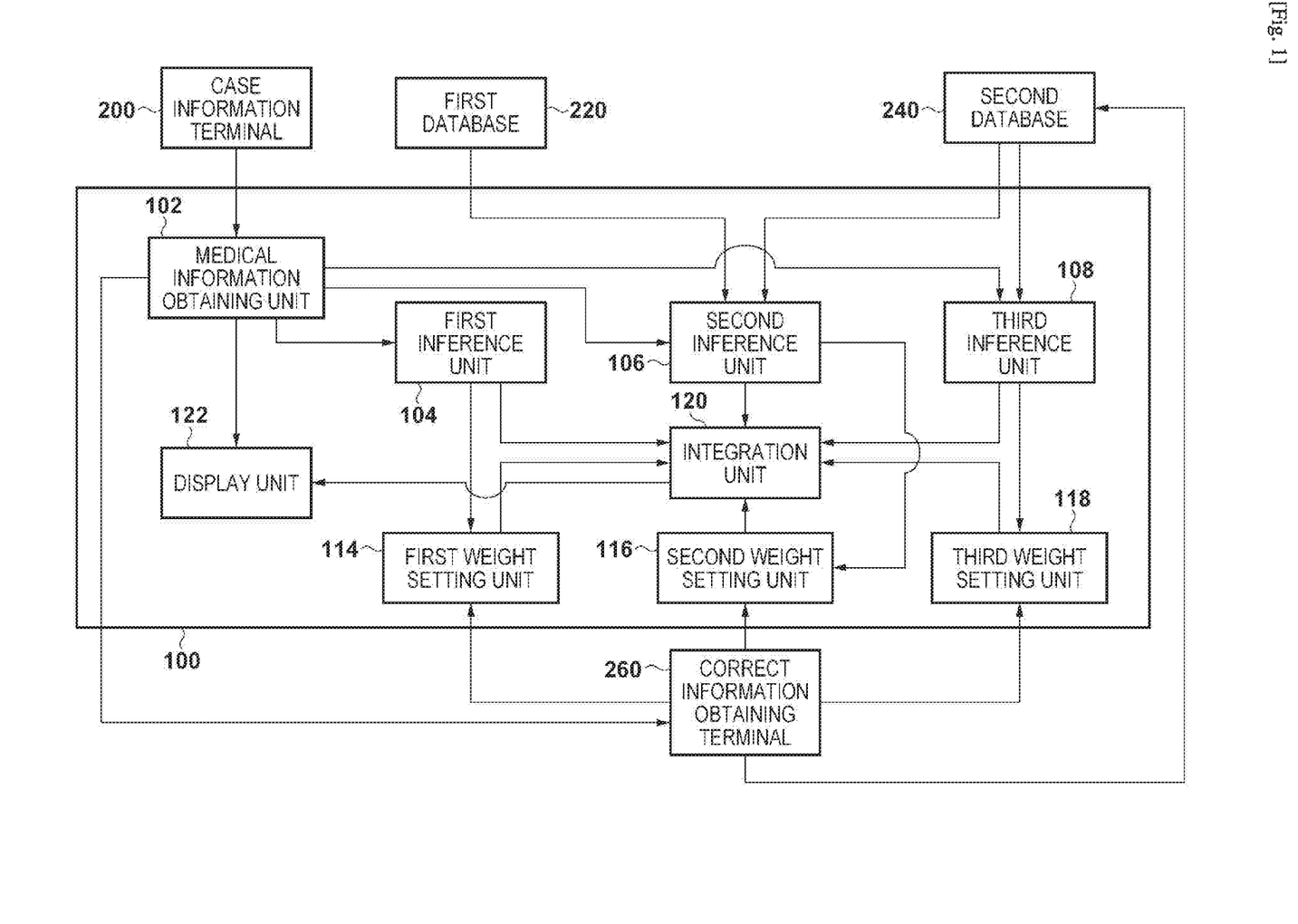
FIG. 1 is a block diagram showing an example of the functional arrangement of a diagnosis support apparatus according to the first embodiment of the present invention.

FIG. 1 is a block diagram showing an example of the functional arrangement of a diagnosis support apparatus 100 according to the first embodiment. The diagnosis support apparatus 100 according to this embodiment is connected to a case information terminal 200, a first database 220, a second database 240, and a correct information obtaining terminal 260.

The case information terminal 200 obtains medical information (medical image information, electronic health record information, and the like) concerning a case as a diagnosis target from a server (not shown). Alternatively, the case information terminal 200 may obtain data from external storage devices such as an FDD, HDD, CD drive, DVD drive, MO drive, and ZIP drive by connecting the external storage devices.

Note that the case information terminal 200 may display these pieces of information on a monitor in a form that allows the user (doctor) to interpret, and obtain image findings input by the user based on the display contents. Both the pieces of information may be obtained, as a matter of course. In this embodiment, assume that the case information terminal 200 obtains, as medical information, the image findings input by the user and the contents and medical image described in the electronic health record. In response to a request from the user, the case information terminal 200 transmits the medical information to the diagnosis support apparatus 100 via a LAN or the like.

The first database 220 and the second database 240 store data formed by sets of pieces of medical information and diagnosis names (that is, correct answers) collected under different conditions, respectively. Assume that data collected under the first condition are stored in the first database 220, and data collected under the second condition are stored in the second database. In this embodiment, the first condition is that data are collected in the first facility, and the second condition is that data are collected in the second facility.

More specifically, assume that the first database 220 stores data in the facility where training data (that is, learning data) are collected. Assume also that the second database 240 stores data (that is, additional data) in the facility where the diagnosis support apparatus 100 is operated. Conditions are not limited to them, as a matter of course. For example, data stored until time H and data stored after time H in the same facility may be stored in the first and second databases, respectively.

Alternatively, data for images captured by different modalities may be stored in the databases, respectively. Then, in response to a request from the diagnosis support apparatus 100, each of the first database 220 and the second database 240 transmits the data to the diagnosis support apparatus 100. Note that in this embodiment, the second database 240 stores new data based on data transmitted from the correct information obtaining terminal 260.

The correct information obtaining terminal 260 obtains, by a user input, a diagnosis name (that is, correct answer) for medical information transmitted from the diagnosis support apparatus 100. Note that this input is desirably performed independently of the processing of the diagnosis support apparatus 100. That is, instead of reflecting the thought of the doctor when support information is presented, the input is desirably performed when the diagnosis name of a case corresponding to the medical information is confirmed. Alternatively, the correct information obtaining terminal 260 may be connected to a server (for example, an electronic health record or PACS) (not shown), and configured to automatically obtain a diagnosis name when the diagnosis name is assigned to the case corresponding to the medical information transmitted from the diagnosis support apparatus 100. The correct information obtaining terminal 260 then transmits a set of the medical information and the diagnosis name to the diagnosis support apparatus 100 and the second database 240. Note that each constituent element connected to the diagnosis support apparatus 100 may be included in the diagnosis support apparatus 100.

The diagnosis support apparatus 100 includes a medical information obtaining unit 102, a first inference unit 104, a second inference unit 106, a third inference unit 108, a first weight setting unit 114, a second weight setting unit 116, a third weight setting unit 118, an integration unit 120, and a display unit 122.

The medical information obtaining unit 102 obtains, as medical information, information transmitted from the case information terminal 200 to the diagnosis support apparatus 100. The medical information obtaining unit 102 transmits the obtained medical information to the first inference unit 104, second inference unit 106, third inference unit 108, display unit 122, and correct information obtaining terminal 260.

Each of the first inference unit 104, second inference unit 106, and third inference unit 108 executes inference concerning an abnormal shadow in a lung as a diagnosis target based on the medical information obtained by the medical information obtaining unit 102. More specifically, in order to indicate a specific one of a plurality of diagnosis names to which an abnormal shadow on a medical image corresponds with high probability, each inference unit calculates a probability (inference result) at which the abnormal shadow corresponds to each of the diagnosis names.

Each of the first inference unit 104, second inference unit 106, and third inference unit 108 outputs the calculated inference result to the integration unit 120 and one of the weight setting units 114, 116, and 118, which corresponds to the inference unit. Note that the Nth weight setting unit corresponds to the Nth inference unit. The second inference unit 106 periodically obtains a set of medical information and a diagnosis name (correct answer) from each of the first database 220 and the second database 240 to update the inference unit, and the third inference unit 108 periodically obtains a set of medical information and a diagnosis name (correct answer) from the second database 240 to update the inference unit. A detailed description thereof will be given later.

Each of the first weight setting unit 114, second weight setting unit 116, and third weight setting unit 118 sets a weight and outputs the set weight to the integration unit 120. Furthermore, each of the first weight setting unit 114, second weight setting unit 116, and third weight setting unit 118 periodically resets the weight based on the inference result calculated by the corresponding inference unit and the data transmitted from the correct information obtaining terminal 260. A detailed description thereof will be given later.

The integration unit 120 integrates the inference results calculated by the first inference unit 104, second inference unit 106, and third inference unit 108. Based on, for example, the weights output from the first to third weight setting units, the integration unit 120 integrates the plurality of inference results calculated by the first inference unit 104, second inference unit 106, and third inference unit 108. The integration unit 120 outputs the integrated inference result to the display unit 122. The display unit 122 displays support information based on the medical information obtained by the medical information obtaining unit 102 and the inference result integrated by the integration unit 120.

Note that at least some of the respective units of the diagnosis support apparatus 100 shown in FIG. 1 may be implemented as independent apparatuses. Alternatively, each unit may be implemented as software to implement the function. In this embodiment, assume that each unit is implemented by software.

Figure 2:
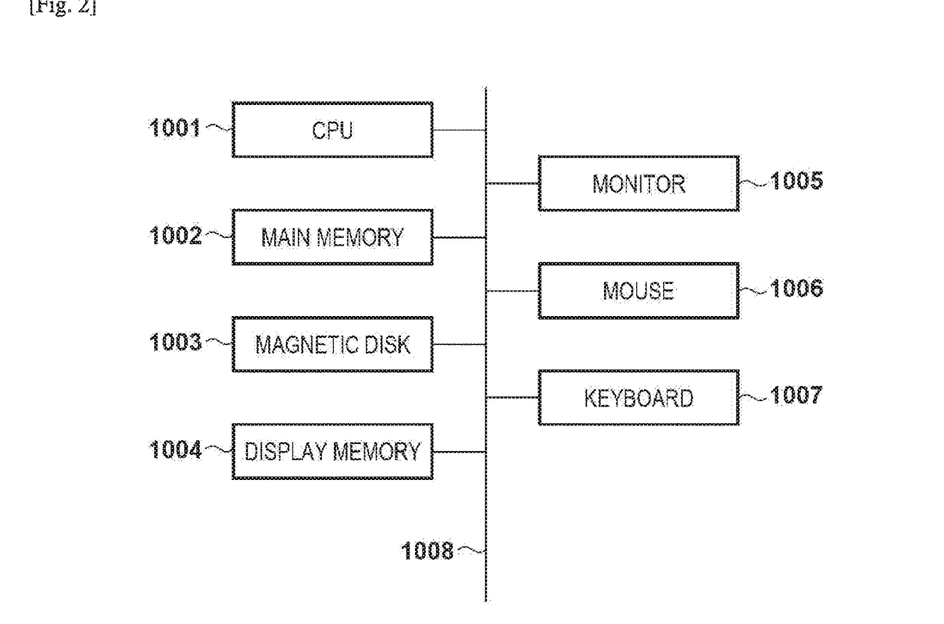
FIG. 2 is a block diagram showing the hardware arrangement of the diagnosis support apparatus according to the first embodiment of the present invention.

FIG. 2 is a block diagram showing an example of the hardware arrangement of the diagnosis support apparatus 100. A CPU 1001 mainly controls the operation of each constituent element. A main memory 1002 stores control programs executed by the CPU 1001, and provides a work area at the time of execution of a program by the CPU 1001. A magnetic disk 1003 stores programs for implementing various kinds of application software including an operating system (OS), device drivers for peripheral devices, and programs for performing processing (to be described later). The CPU 1001 implements the functions (software) of the diagnosis support apparatus 100 shown in FIG. 1 and the processing of a flowchart (to be described later) by executing the programs stored in the main memory 1002 and the magnetic disk 1003.

A display memory 1004 temporarily stores display data. A monitor 1005 is, for example, a CRT monitor or a liquid crystal monitor, and displays images, text, and the like based on display data output from the display memory 1004. A mouse 1006 and a keyboard 1007 are used to accept an input such as a pointing input and an input of characters and the like by the user. The respective constituent elements described above are communicably connected to each other via a common bus 1008.

<Processing of Diagnosis Support Apparatus>

Figure 3:
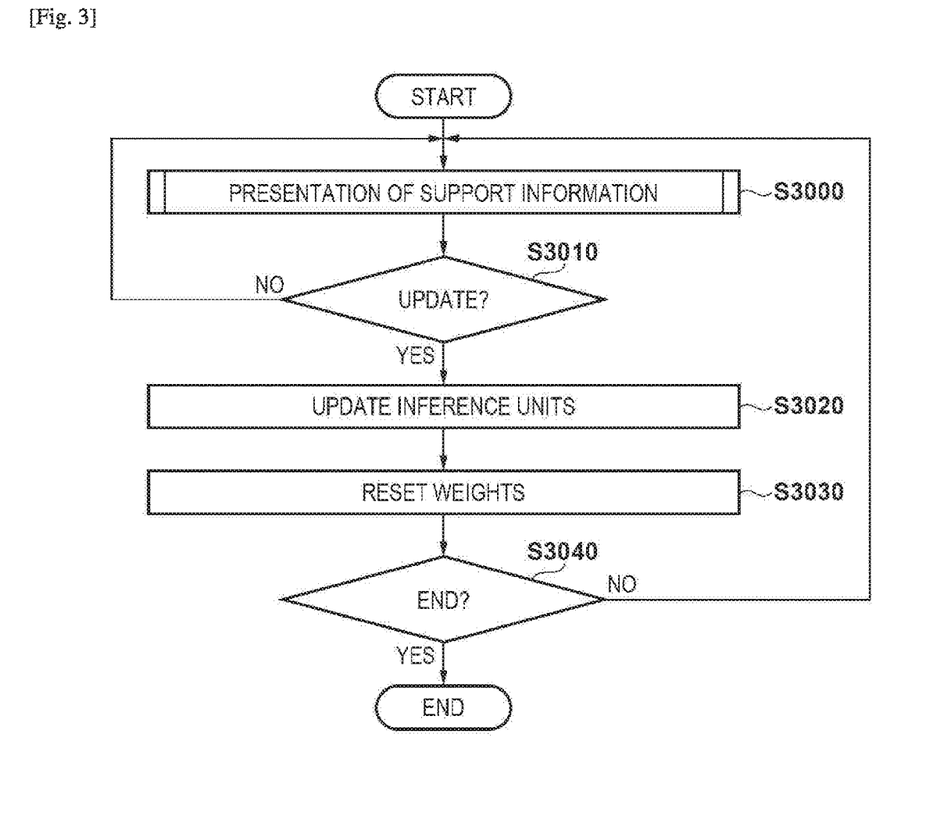
FIG. 3 is a flowchart illustrating an example of the processing of the diagnosis support apparatus according to the first embodiment of the present invention.
Figure 4:
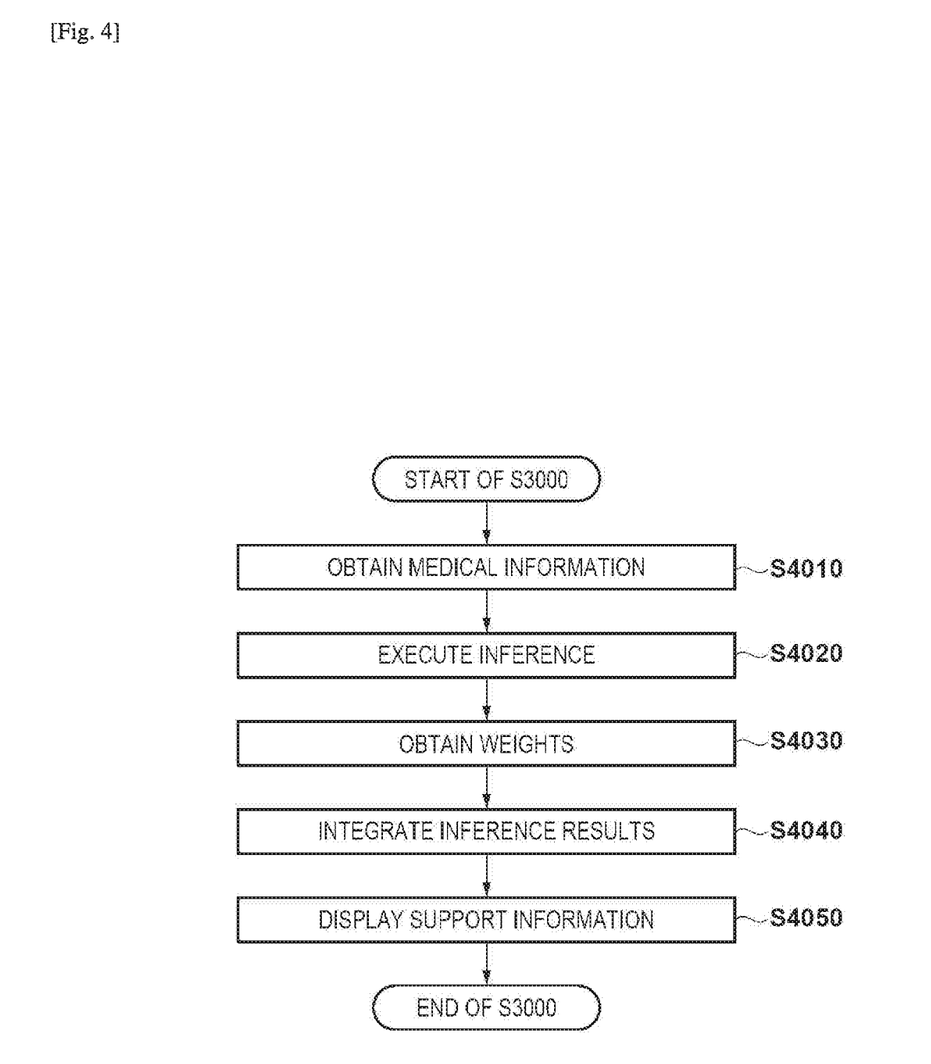
FIG. 4 is a flowchart illustrating an example of processing in step S3000 according to the first embodiment of the present invention.

The overall processing performed by the diagnosis support apparatus 100 will be described with reference to flowcharts shown in FIGS. 3 and 4. FIGS. 3 and 4 are flowcharts illustrating an example of the processing performed by the diagnosis support apparatus 100. In this embodiment, the processing shown in FIGS. 3 and 4 is implemented when the CPU 1001 executes programs, stored in the main memory 1002, for implementing the functions of the respective units.

In the following description, a set of pieces of medical information will be written as E, and a set of diagnosis names will be written as D. In this embodiment, a diagnosis name takes three values respectively representing a primary lung cancer, a lung cancer metastasis, and a benign lesion, which will be respectively written as D1, D2, and D3. The inference probability of a diagnosis name Dd (d=1, 2, 3) when E is input to each of the first inference unit 104, second inference unit 106, and third inference unit 108 will be written as $Pn(Dd|E)$ (n=1, 2, 3) (corresponding to the Nth inference unit). In addition, the weight set by each of the first to third weight setting units will be written as Wn (n=1, 2, 3) (corresponding to the Nth weight setting unit).

<Step S3000>

In step S3000, the diagnosis support apparatus 100 presents support information based on medical information input to the diagnosis support apparatus 100. The flowchart of FIG. 4 shows details of the processing in step S3000.

In step S4010, the medical information obtaining unit 102 obtains the medical information input to the diagnosis support apparatus 100. As described above, in this embodiment, assume that the medical information includes a medical image, image findings, and clinical information. The medical information obtaining unit 102 transmits the medical information to the correct information obtaining terminal 260.

In step S4020, each of the first inference unit 104, second inference unit 106, and third inference unit 108 executes inference concerning an abnormal shadow in a lung as a diagnosis target based on the medical information obtained in step S4010. As a method of performing inference (inference method) at this time, it is possible to use one of various existing methods such as a Bayesian network, neural network, and support vector machine. This embodiment uses the Bayesian network as an inference method executed by each of the first inference unit 104, second inference unit 106, and third inference unit 108. The Bayesian network is an inference model using conditional probabilities. It is possible to obtain the inference probability of each diagnosis name when information is input (the probability of the case being each diagnosis name, which is also called a posterior probability). In this embodiment, the inference probability (that is, $Pn(Dd|E)$) of each diagnosis name D1, D2, or D3 of the abnormal shadow is obtained.

In step S4030, each of the first weight setting unit 114, second weight setting unit 116, and third weight setting unit 118 outputs the set weight. This weight is reset in step S3030 (to be described later). In this embodiment, however, the initial values are set, as given by W1=1.0 and W2=W3=0. Initial values are not limited to them, as a matter of course.

The diagnosis support apparatus 100 holds the inference results obtained in step S4020. For example, the diagnosis support apparatus 100 may save the inference results in, for example, a storage unit (not shown). The held contents are used to reset the weights in step S3030.

In step S4040, the integration unit 120 integrates a plurality of inference results based on the inference results obtained in step S4020 and the weights obtained in step S4030. In this embodiment, the integration unit 120 integrates the inference probabilities P(Dd) of the diagnosis names Dd, given by:

[Math. 1]

$$P(D_d) = \frac{\sum_n W_n P(D_d | E)}{\sum_n W_n} \quad (1)$$

In step S4050, the display unit 122 presents support information based on the medical information obtained in step S4010 and the inference result integrated in step S4040. In this embodiment, the display unit 122 presents the integrated inference result as support information. When this step ends, the process returns to the flowchart of FIG. 3 to execute processing in step S3010.

<Step S3010>

In step S3010, the diagnosis support apparatus 100 determines whether to update the second inference unit 106 and the third inference unit 108 and whether to reset the weights of the first weight setting unit 114, second weight setting unit 116, and third weight setting unit 118 in accordance with an update condition. The diagnosis support apparatus 100 may determine to perform update processing every time a given time elapses after the last update processing (every time an elapsed time after the last update processing reaches a predetermined value). Alternatively, the number of times the processing in step S3000 is executed may be stored, and when the execution count (the number of cases for which diagnosis support is performed) reaches a predetermined value, the diagnosis support apparatus 100 may determine to perform update processing. In this embodiment, assume that the diagnosis support apparatus 100 determines to perform update processing when the number of sets of pieces of medical information and diagnosis names transmitted from the correct information obtaining terminal 260 to the diagnosis support apparatus 100 and the second database 240 becomes equal to or larger than a predetermined value (for example, 20). That is, the diagnosis support apparatus 100 determines to perform update processing when the number of data added after the last update processing becomes equal to or larger than a predetermined value. If it is determined to perform update processing, processing in step S3020 is executed; otherwise, the process returns to the processing in step S3000.

Note that these determination processes may be separately or simultaneously performed. In this embodiment, assume that these two determination processes are simultaneously performed. That is, the inference unit update determination processing and the weight update determination processing always provide the same determination result. A processing example when the determination processes are separately executed will be described later in a modification.

<Step S3020>

In step S3020, the second inference unit 106 obtains a set of medical information and a diagnosis name from each of the first database 220 and the second database 240, and updates the second inference unit 106. The third inference unit 108 obtains a set of medical information and a diagnosis name from the second database 240, and updates the third inference unit. Note that the second inference unit 106 and the third inference unit 108 may obtain only a set (that is, additional data) of medical information and a medical name newly transmitted from the correct information obtaining terminal 260 to the second database 240. In this case, sets of pieces of medical information and diagnosis names obtained until now are desirably held. In this embodiment, assume that only a set of medical information and a diagnosis name newly transmitted to the second database 240 is obtained.

To update the inference unit, only parameters related to the current inference unit may be changed, or the type of medical information (that is, variables) to be used may be changed by performing feature amount selection. In the example of the Bayesian network, the former corresponds to the change of the conditional probability between the variables and the latter corresponds to the change of connection (cause-and-effect relationship) between the variables. In this update processing, cross-validation may be performed using data obtained by adding new data to currently held data, thereby maximizing the performance of the inference unit. Alternatively, the update processing may be performed to maximize the performance of the inference unit for new data using the currently held data.

Figure 5:
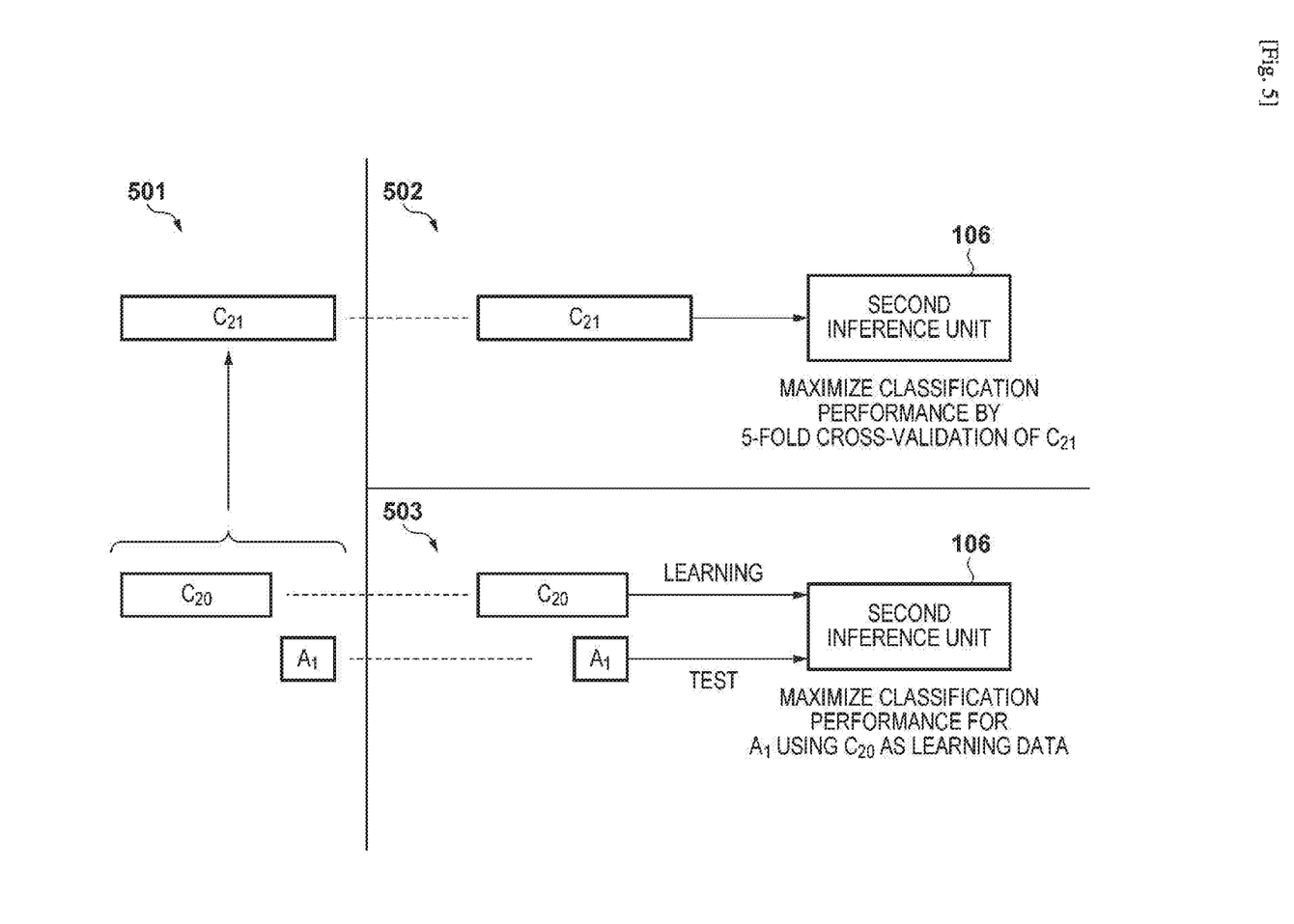
FIG. 5 is a view schematically showing update of an inference unit according to the first embodiment of the present invention.

FIG. 5 is a view schematically showing update of the second inference unit 106. Reference symbol C20 denotes a set of medical information and a diagnosis name stored in each of the first database 220 and the second database 240 in the initial state (T=0 where T represents the number of times it is determined to perform update processing in step S3010). Note that for T=0, there may be no data stored in the second database 240 (that is, data is stored in only the first database). Reference symbol A1 denotes a set of medical information and a diagnosis name, which is obtained in this step and newly transmitted to the second database 240.

In an example shown in 501 and 502 of FIG. 5, the inference unit is updated by cross-validation (in this example, 5-fold cross-validation) using data C21 obtained by adding the data A1 to the data C20. In this case, the inference unit is updated to provide optimum classification results for all data which can be used in the current inference unit. That is, the inference unit is updated to have an improved generalization performance.

In an example shown in 501 and 503 of FIG. 5, the inference unit is updated by using the data C20 as learning data and the data A1 as test data. In this case, the inference unit is updated to provide an optimum classification result for new data using the data held until now. That is, the inference unit is updated to specialize in the new data. In other words, if the collection condition of the held data is different from that of the new data, the inference unit is updated to provide an optimum classification result for data collected under the collection condition of the new data.

<Step S3030>

In step S3030, each of the first weight setting unit 114, second weight setting unit 116, and third weight setting unit 118 resets the weight based on the inference result of the corresponding inference unit obtained in step S4020 and the sets of the pieces of medical information and diagnosis names transmitted from the correct information obtaining terminal 260.

The weight may be determined based on the number (T) of times step S3010 is executed and it is determined to perform update processing. For example, as T is larger, the third inference unit may be considered more important. More specifically, the first weight setting unit 114 may reset the weight to a smaller value as T is larger, the second weight setting unit 116 may not reset the weight, and the third weight setting unit 118 may reset the weight to a larger value as T is larger. The weights may be set by another method, as a matter of course. In this embodiment, assume that based on the inference result obtained in step S4020 and the diagnosis names transmitted from the correct information obtaining terminal 260, the weights are reset depending on the degree of accuracy of the inference result obtained in step S4020. That is, the first to third inference performances at the time of T are reset as the weights.

Figure 6:
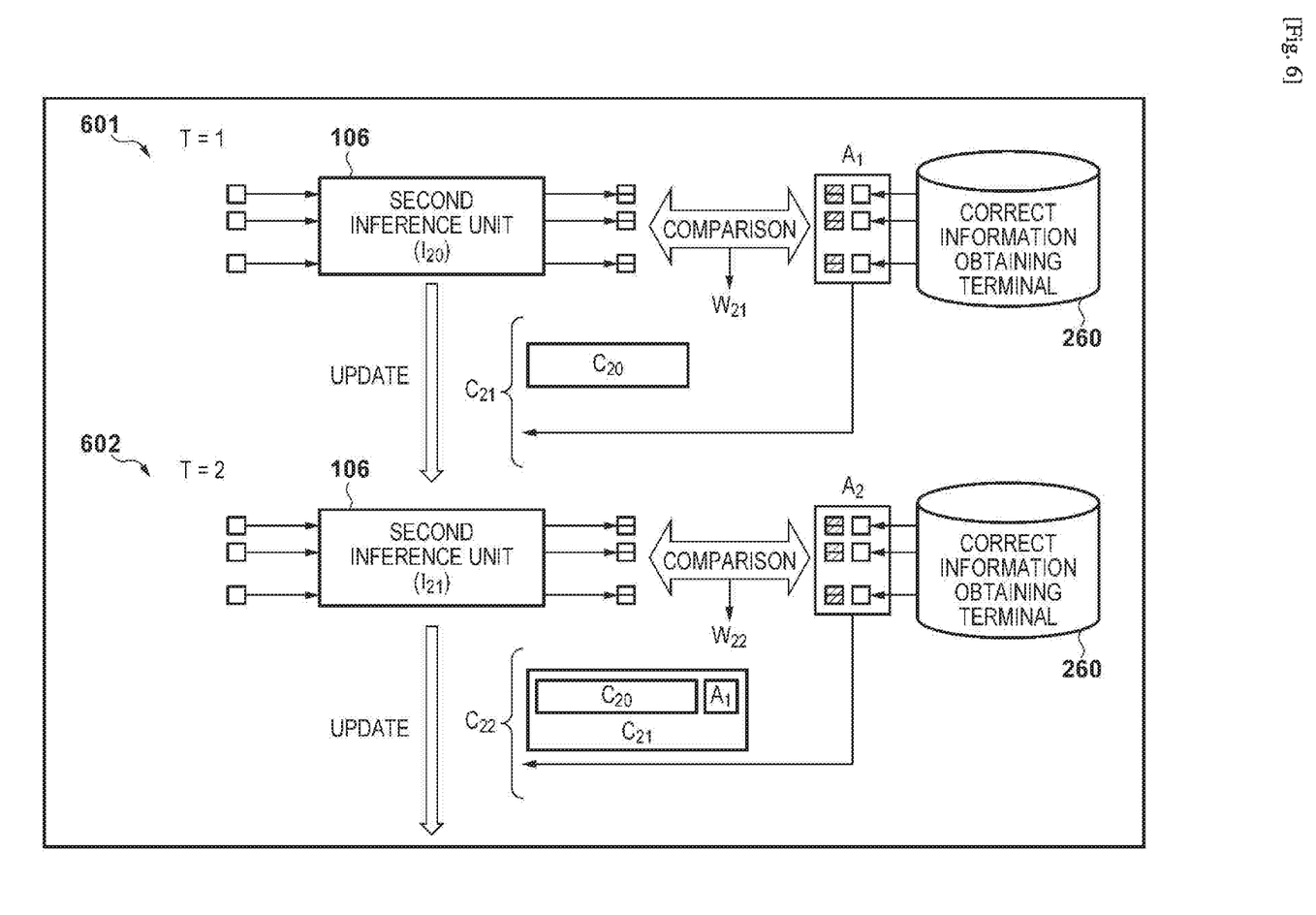
FIG. 6 is a view schematically showing reset of a weight according to the first embodiment of the present invention.

FIG. 6 is a view schematically showing reset of the weight of the second weight setting unit 116. In FIG. 6, 601 shows a state for T=1 and 602 shows a state for T=2. Furthermore, I2T and W2T represent the second inference unit and the second weight at the time of T, respectively. As shown in 601, for T=1, the inference result (that is, the inference result obtained in step S4020) of A1 by the inference unit (that is, the inference unit I20 at the time of T−1) before the update processing is compared with the diagnosis name of A1. Based on the comparison result, the weight W21 for T=1 is reset as the weight of the second weight setting unit 116.

For this weight, the degree of matching (correct answer ratio) between a diagnosis name with the highest inference probability and a correct diagnosis name may be used or an average log-likelihood using the inference probability for the correct diagnosis name may be used. Similarly, as shown in 602, for T=2, the inference result is compared with the correct diagnosis name for the inference unit I21 before the update processing, and the weight W22 is calculated, and reset as the weight of the second weight setting unit 116.

<Step S3040>

In step S3040, the diagnosis support apparatus 100 determines whether to end the processing. For example, it may be determined whether to end the processing, based on the number (T) of times step S3010 is executed and it is determined to perform update processing. If the number (T) of times has reached a predetermined value, it may be determined to end the processing. If it is not determined to end the processing, the process returns to step S3000. The processing shown in FIGS. 3 and 4 is executed according to the above procedure.

Figure 7A:
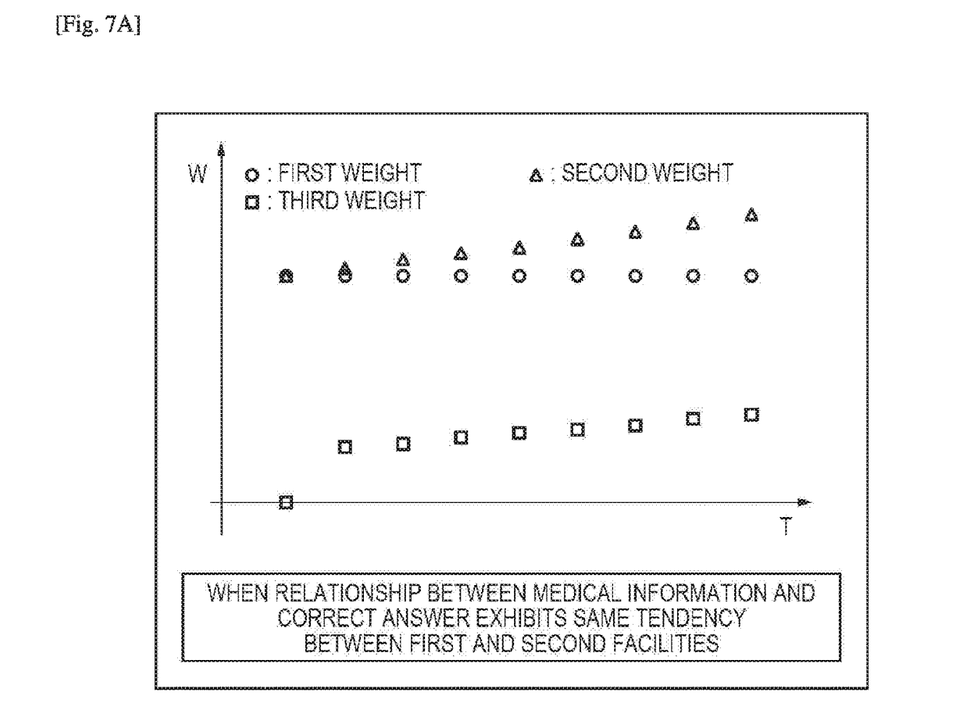
FIG. 7A is a graph schematically showing changes in weights when data are collected in different facilities according to the first embodiment of the present invention.
Figure 7B:
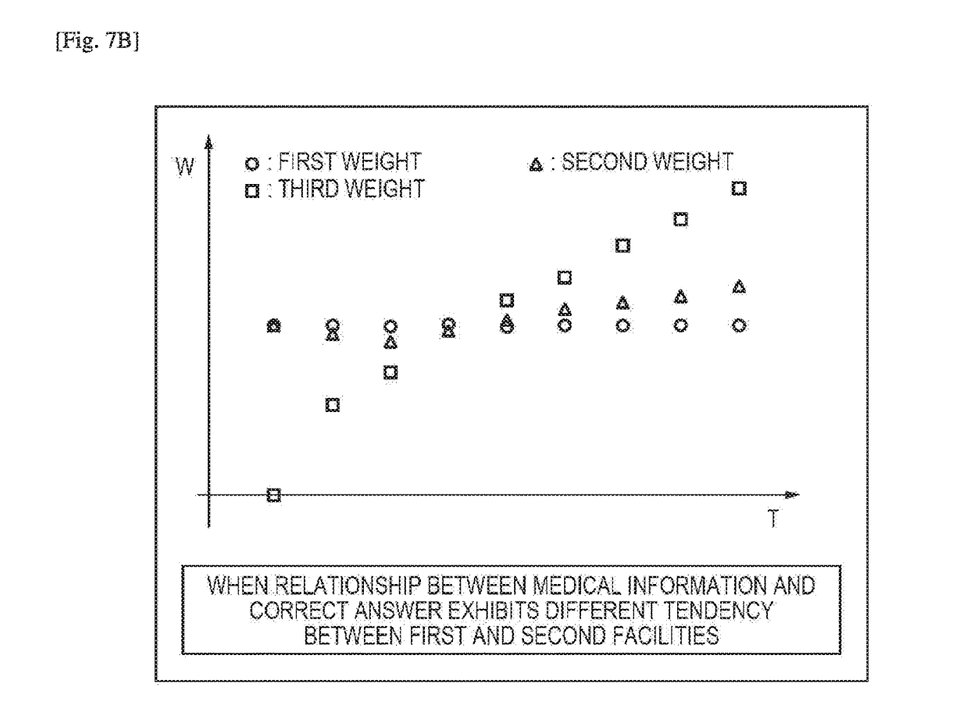
FIG. 7B is a graph schematically showing changes in weights when data are collected in different facilities according to the first embodiment of the present invention.

FIGS. 7A and 7B are graphs each schematically showing reset of the weights by the first weight setting unit 114, second weight setting unit 116, and third weight setting unit 118 when the diagnosis support apparatus 100 is operated in the second facility under the condition that data in the first database 220 are collected in the first facility and data in the second database 240 are collected in the second facility. FIG. 7A shows a case in which the relationship between medical information and a correct answer (diagnosis name) exhibits the same tendency between the first and second facilities. On the other hand, FIG. 7B shows a case in which the relationship between medical information and a correct answer (diagnosis name) exhibits a different tendency between the first and second facilities. T represents the number of times the inference units and the weights are reset (that is, the number of times step S3010 is executed and it is determined to perform update processing), and W represents the weight. Assume that the above-described correct answer ratio is used as the weight. That is, the weight is equal to the expected value of an inference result for new data.

As shown in FIG. 7A, if the relationship between the medical information and a correct answer exhibits the same tendency, the weight of the first inference unit 104 remains at high level, and the weight of the second inference unit 106 increases since the performance of the inference unit improves as the number of data increases. On the other hand, the weight of the third inference unit 108 is not considered important at first since the number of data is small and thus the performance of the inference unit is low. That is, in the case of FIG. 7A, the inference results are integrated so that the second inference unit 106 is considered important.

On the other hand, as shown in FIG. 7B, if the relationship between medical information and a correct answer exhibits a different tendency, the weight of the first inference unit 104 remains at low level. The weight of the second inference unit 106 increases as data in the second facility increases. The weight of the third inference unit 108 remains small while the inference unit specializes in data in the second facility since the inference unit is formed using data in the second facility, and the number of data is small. However, the weight becomes larger as the number of data increases. That is, in the case of FIG. 7B, the outputs of the plurality of inference units are used at first, and the inference results are integrated so that the third inference unit 108 is considered important in the second half.

Update of the inference units and setting of the weights are automatically performed. Thus, even if the relationship between medical information and a correct answer exhibits any tendency between the first and second facilities, the user can automatically obtain a result of integrating appropriate inference results. Consequently, when a diagnosis support apparatus in which learning data are formed under a given condition (for example, a given facility) is operated under another condition (another facility), it is possible to smoothly operate the diagnosis support apparatus.

According to this embodiment, the diagnosis support apparatus 100 updates the inference units and resets the weights in accordance with a data collection status. This allows the user to obtain a result of integrating appropriate inference results without considering the relationship between collected data. Thus, even if the collection source of data is different from the operation destination of the apparatus, it is possible to smoothly operate the diagnosis support apparatus.

<First Modification>

In this embodiment, in step S3010, the inference unit update determination processing and the weight update determination processing are simultaneously performed. However, these processes may be separately performed. In this case, if it is determined to update the inference units or the weights, the processes in step S3020 and subsequent steps are performed. More specifically, if it is determined to update the inference units, the processing in step S3020 is performed. If it is determined to update the weights, the processing in step S3030 is performed. In this case, assume that the processing step corresponding to the inference units or the weights which have been determined not to be updated is not executed. For example, if it is determined to update only the inference units, the processing in step S3020 is executed, and then the processing in step S3040 is executed.

<Second Modification>

In this embodiment, in step S3020, only the second inference unit 106 and the third inference unit 108 are updated. However, the first inference unit 104 may also be updated. For example, the classification performance for AT (T represents the number of times it is determined in step S3010 to perform update processing) may be maximized by using, as learning data, the data stored in the first database 220. Alternatively, the classification performance for data A1 to AT may be maximized.

Furthermore, the first database 220 may be communicably connected to another diagnosis support apparatus to update the data in the first database 220. In this case, the collection condition of data added to the first database 220 is desirably the same as that of the data stored in the first database 220.

Note that the above modifications are also applicable in the following embodiments.

Second Embodiment

In the first embodiment, the inference units are updated using the newly obtained data. A diagnosis support apparatus 100 according to this embodiment updates inference units by utilizing the inference units in the past using transition of newly obtained data.

Note that the functional arrangement of the diagnosis support apparatus 100 according to this embodiment is the same as that shown in FIG. 1 of the first embodiment. The hardware arrangement of the diagnosis support apparatus 100 is the same as that shown in FIG. 2 of the first embodiment. That is, the function (software) of the diagnosis support apparatus 100 and the processing of a flowchart according to this embodiment are implemented when a CPU 1001 executes programs stored in a main memory 1002 and a magnetic disk 1003. A flowchart for explaining the overall processing performed by the diagnosis support apparatus 100 is the same as that shown in FIG. 3. However, part of the processing is different from the first embodiment. The difference from the first embodiment in the overall processing performed by the diagnosis support apparatus 100 according to this embodiment will be described with reference to the flowchart of FIG. 3.

Processes in steps S3000 and S3010 are the same as those in the first embodiment. In step S3020, a second inference unit 106 obtains a set of medical information and a diagnosis name from each of a first database 220 and a second database 240, and updates the second inference unit 106 based on transition of data collected in the second database 240. In addition, a third inference unit 108 obtains a set of medical information and a diagnosis name from the second database 240, and updates the third inference unit based on transition of data collected in the second database 240. The inference units before the update processing are saved in a storage unit (not shown).

Figure 8:
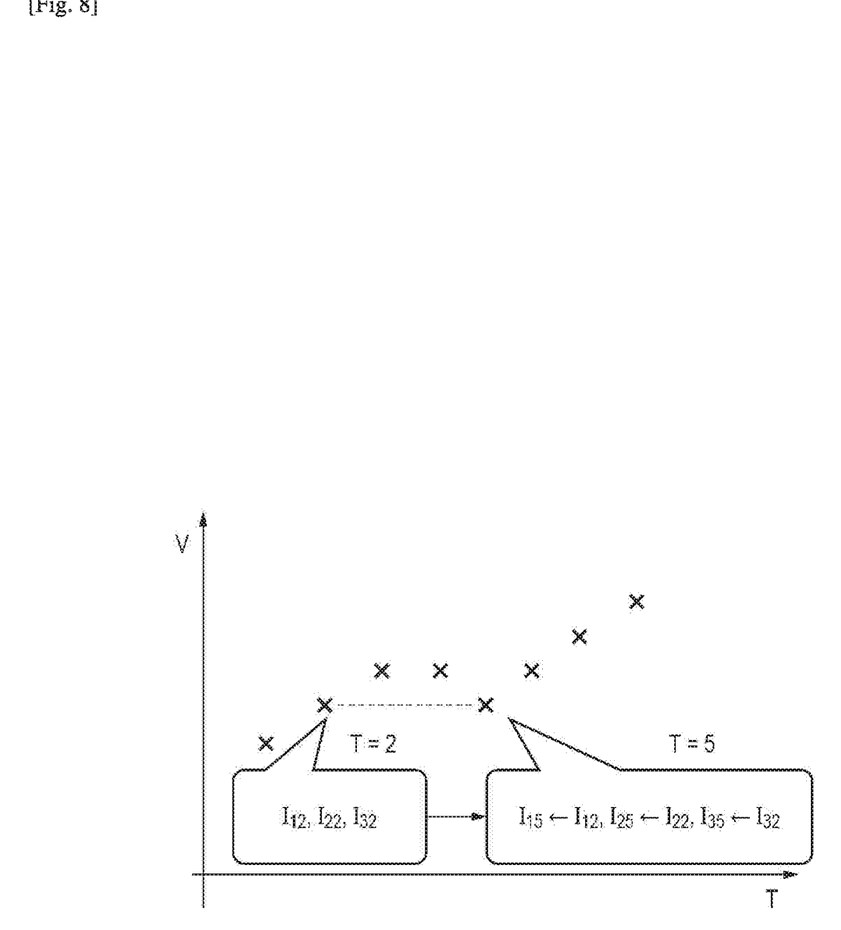
FIG. 8 is a graph schematically showing transition of data according to the second embodiment of the present invention.

FIG. 8 schematically shows the processing in step S3020 according to this embodiment. V represents a position on the data space of data. V for T will be represented by VT hereinafter. The position on the space is presented by a vector created from the median (average value) or variance of pieces of medical information included in data (AT). In this embodiment, a vector Vt for T=t and vectors before T=t (that is, vectors V1 to Vt−1 for T=1 to T−1) are used. More specifically, the inference units are updated and the weights are reset in accordance with whether the vectors match (that is, whether data in AT match).

A description will be provided below using a practical example. In FIG. 8, for T=2, since there is no position on the space before T=2, which matches V2, the inference units are updated and the weights are reset by the same processing as in step S3020 of the first embodiment. On the other hand, for T=5, there exists V2 as a position on the space, which matches V5. In this case, it is determined that the inference units and weights for V2 are appropriate as the inference units and weights for V5, and then the inference units are updated to the same ones as those for V2 and the weights are reset to the same ones as those for V2. That is, with respect to the second inference unit 106, a second inference unit I25 for T=5 is updated to a second inference unit I22 for T=2. Similarly, a third inference unit I35 for T=5 is updated to a third inference unit I32 for T=2. Note that if the first inference unit 104 is not updated as in this embodiment, a first inference unit I15 for T=5 is identical to a first inference unit I12 for T=2.

Note that the above example shows a case in which the vectors match. However, the vectors do not necessarily match. For example, the similarities of the vectors may be calculated, and then the inference units and weights for T of a vector having the highest similarity may be used to update the inference units and reset the weights. In this case, a threshold may be set, and if the similarity does not exceed the threshold, the inference units may be updated by the same method as in the first embodiment.

Processes in steps S3030 and S3040 are the same as those in the first embodiment.

According to this embodiment, the diagnosis support apparatus 100 updates the inference units in accordance with the data transition status. A first weight setting unit 114, a second weight setting unit 116, and a third weight setting unit 118 reset the first, second, and third weights at the time of the Tth update processing using the first, second, and third weights at the time of at least one of the (T−1) update processes (T=1 to T−1) corresponding to data similar to data newly collected at the time of the Tth update processing. Furthermore, a first inference unit 104, a second inference unit 106, and a third inference unit 108 update the first inference unit 104, second inference unit 106, and third inference unit 108 at the time of the Tth update processing using the first inference unit 104, second inference unit 106, and third inference unit 108 at the time of at least one of the (T−1) update processes (T=1 to T−1) corresponding to data similar to data newly collected at the time of the Tth update processing.

This can quickly update the inference units using the inference units at the time of the same data distribution even if the data distribution is different depending on a data collection timing. Thus, the user can obtain a result of integrating appropriate inference results without considering a distribution depending on the collection timing of collected data. This allows the user to smoothly operate the diagnosis support apparatus.

<First Modification>

In this embodiment, in step S3020, the second inference unit 106 and the third inference unit 108 update the inference units using the inference units at a vector which matches a vector indicating data (or has the highest similarity). However, the number of target vectors is not necessarily one. For example, all vectors each having a similarity equal to or larger than a given threshold may be selected, and new inference units may be set using the inference units at the vectors. For example, if the similarities of V1, V2, and V3 with V4 are respectively 0.6, 0.8, and 0.9 and the threshold is 0.8, the inference units at V4 are updated using the inference units at V2 and V3. In this case, the inference units at V4 may be updated by inference units which output the averages of the outputs of the inference units at V2 and V3 or inference units which output weighted averages based on the similarities.

<Second Modification>

In this embodiment, in step S3020, only the inference units are updated based on transition of data. However, similarly, in step S3030, the weights of the first to third weight setting units may be updated based on transition of data. That is, the weights at a vector which matches the vector (or has the highest similarity) may be reset as the weights.

Third Embodiment

In the first and second embodiments, support information is provided using the diagnosis support apparatus 100 installed in a local environment. A diagnosis support apparatus 100 according to this embodiment is different from that in each of the first and second embodiments in that the diagnosis support apparatus 100 is installed in an environment different from a use location, and connected to the use location using a communication unit such as optical fiber communication, thereby providing support information by a client-server system.

Figure 9:
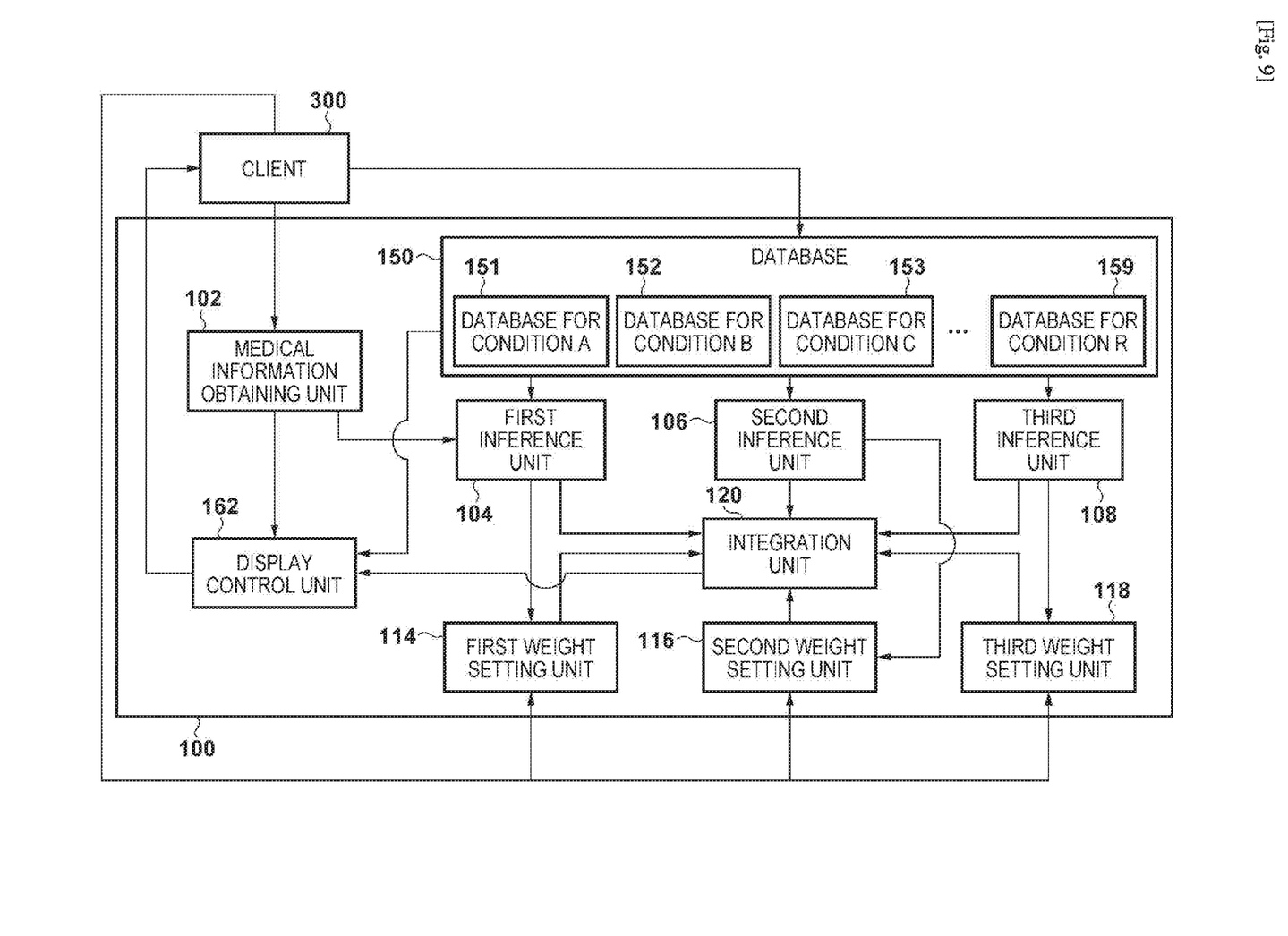
FIG. 9 is a block diagram showing an example of the functional arrangement of a diagnosis support apparatus according to the third embodiment of the present invention.

FIG. 9 is a block diagram showing an example of the functional arrangement of the diagnosis support apparatus 100 according to the third embodiment. Note that the functional arrangement of the diagnosis support apparatus 100 according to this embodiment is partially common to that in the first embodiment. The difference from the first embodiment will be described below.

The diagnosis support apparatus 100 according to this embodiment is connected to a client 300. The client 300 performs display based on contents transmitted from a display control unit 162 (to be described later). An operation (for example, the input of medical information) performed by the client 300 is transmitted to the diagnosis support apparatus 100, and processed in the diagnosis support apparatus 100.

Databases 150 include databases 151 to 159 for conditions A to R, and store data for the different conditions. More specifically, a medical image is obtained from an imaging apparatus (not shown) connected to the diagnosis support apparatus 100. Furthermore, data of sets of pieces of medical information and correct answers transmitted from the client 300 are saved. The data are saved in the different databases for the respective conditions (for example, facilities in each of which the client 300 and the imaging apparatus (not shown) are installed). Alternatively, a condition may be described as one of records forming data, and the data may be saved in one database.

The display control unit 162 receives an output from an integration unit 120 or outputs from the databases 150, and controls contents to be displayed on the client 300.

The hardware arrangement of the diagnosis support apparatus 100 is the same as that shown in FIG. 2 of the first embodiment. That is, the function (software) of the diagnosis support apparatus 100 and the processing of a flowchart according to this embodiment are implemented when a CPU 1001 executes programs stored in a main memory 1002 and a magnetic disk 1003. Flowcharts for explaining the overall processing performed by the diagnosis support apparatus 100 are the same as those shown in FIGS. 3 and 4. However, part of the processing is different from the first embodiment. The difference from the first embodiment in the overall processing performed by the diagnosis support apparatus 100 according to this embodiment will be described with reference to the flowcharts of FIGS. 3 and 4.

Processing in step S3000 is the same as that in the first embodiment except that, in step S4050, the display control unit 162 controls contents to be displayed on the client 300, and displays them on the display unit of the client 300.

Processing in step S3010 is the same as that in the first embodiment. In step S3020, a second inference unit 106 and a third inference unit 108 obtain, from the databases 150, data (sets of pieces of medical information and diagnosis names) considering a condition (for example, a facility where the client 300 is installed) about the client 300, and updates the respective inference units. For example, if condition B is "a facility where the client 300 is installed", the second inference unit 106 obtains data from all the databases 150, and the third inference unit 108 obtains data from the database 152 for condition B. The inference units are updated by the same method as the inference unit update method described in the first embodiment. That is, in the third embodiment, the first condition is that "data are collected in a facility other than that where the client 300 is installed" and the second condition is that "data are collected in the facility where the client 300 is installed".

Note that a first inference unit 104 may also update the inference unit by the method described in the second modification of the first embodiment. In this case, the inference unit is updated using data satisfying the first condition.

Processing in step S3030 is the same as that in the first embodiment except that sets of pieces of medical information and diagnosis names are transmitted from not a correct information obtaining terminal 260 but the client 300.

Processing in step S3040 is the same as that in the first embodiment.

According to this embodiment, the diagnosis support apparatus 100 accepts an operation from a client connected by a communication unit such as an optical fiber, and provides support information. This allows the user to obtain a result of integrating appropriate inference results without considering the location where the diagnosis support apparatus 100 is installed. Thus, the user can smoothly operate the diagnosis support apparatus.

According to the present invention, it is possible to provide a technique in which when a diagnosis support apparatus formed under a given condition is operated under another condition, the diagnosis support apparatus is smoothly operated.

Other Embodiments

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2016-039197, filed Mar. 1, 2016, which is hereby incorporated by reference wherein in its entirety.

The invention claimed is:

1. A diagnosis support apparatus comprising:
a memory storing a program; and
one or more processors which, by executing the program, function as:
a first inference unit configured to perform inference concerning a diagnosis using data collected under a first condition;
a second inference unit configured to perform inference concerning the diagnosis using the data collected under the first condition and data collected under a second condition different from the first condition;
a third inference unit configured to perform inference concerning the diagnosis using the data collected under the second condition; and
an integration unit configured to integrate inference results of the first inference unit, the second inference unit, and the third inference unit using a first weight, a second weight, and a third weight respectively corresponding to the first inference unit, the second inference unit, and the third inference unit.

2. The apparatus according to claim 1, wherein the one or more processors further function as:
a first weight setting unit, a second weight setting unit, and a third weight setting unit configured to set the first weight, the second weight, and the third weight respectively corresponding to the first inference unit, the second inference unit, and the third inference unit.

3. The apparatus according to claim 1, wherein the one or more processors further function as:
a determination unit configured to determine whether a predetermined update condition is satisfied,
wherein if the determination unit determines that the predetermined update condition is satisfied, the second inference unit and the third inference unit respectively update the second inference unit and the third inference unit.

4. The apparatus according to claim 3, wherein the second inference unit updates the second inference unit based on new data collected under the first condition and an externally obtained correct diagnosis name, and new data collected under the second condition and an externally obtained correct diagnosis name.

5. The apparatus according to claim 3, wherein the third inference unit updates the third inference unit based on new data collected under the second condition and an externally obtained correct diagnosis name.

6. The apparatus according to claim 3, wherein if the determination unit determines that the predetermined update condition is satisfied, the first weight setting unit, the second weight setting unit, and the third weight setting unit respectively reset the first weight, the second weight, and the third weight.

7. The apparatus according to claim 6, wherein the first weight setting unit, the second weight setting unit, and the third weight setting unit respectively reset the first weight, the second weight, and the third weight based on the inference results of the first inference unit, the second inference unit, and the third inference unit and information representing the externally obtained correct diagnosis names.

8. The apparatus according to claim 6, wherein the first weight setting unit, the second weight setting unit, and the third weight setting unit respectively reset, as the first weight, the second weight, and the third weight, inference performances of the first inference unit, the second inference unit, and the third inference unit at the time of last update processing.

9. The apparatus according to claim 6, wherein the first weight setting unit, the second weight setting unit, and the third weight setting unit respectively reset the first weight, the second weight, and the third weight based on the number of times the determination unit determines that the predetermined update condition is satisfied.

10. The apparatus according to claim 3, wherein the predetermined update condition is that an elapsed time after the last update processing reaches a predetermined value.

11. The apparatus according to claim 3, wherein the predetermined update condition is that the number of data newly collected after the last update processing reaches a predetermined value.

12. The apparatus according to claim 1, wherein the first weight setting unit, the second weight setting unit, and the third weight setting unit respectively reset the first weight, the second weight, and the third weight at the time of Tth update processing using the first weight, the second weight, and the third weight at the time of at least one of the (T-1) update processes (T=1 to T-1) corresponding to data similar to data newly collected at the time of the Tth update processing.

13. The apparatus according to claim 1, wherein the first inference unit, the second inference unit, and the third inference unit respectively update the first inference unit, the second inference unit, and the third inference unit at the time of Tth update processing using the first inference unit, the second inference unit, and the third inference unit at the time of at least one of the (T-1) update processes (T=1 to T-1) corresponding to data similar to data newly collected at the time of the Tth update processing.

14. The apparatus according to claim 1, wherein the first condition is that data are collected in at least one facility, and the second condition is that data are collected in at least one facility other than the at least one facility.

15. The apparatus according to claim 14, wherein
the diagnosis support apparatus is connected, by a communication unit, to the at least one facility related to the first condition and the at least one facility related to the second condition, and
the diagnosis support apparatus has a client-server relationship with the at least one facility related to the first condition and the at least one facility related to the second condition.

16. The apparatus according to claim 1, further comprising:
a display control unit configured to display, on a display unit, as support information of the diagnosis, an inference result integrated by the integration unit.

17. A control method for a diagnosis support apparatus having a memory storing a program and one or more processors that, by executing the program, function as a first inference unit, a second inference using, and a third inference unit, comprising:
causing the first inference unit to perform inference concerning a diagnosis using data collected under a first condition;
causing the second inference unit to perform inference concerning the diagnosis using the data collected under the first condition and data collected under a second condition different from the first condition;

causing the third inference unit to perform inference concerning the diagnosis using the data collected under the second condition; and integrating, using a first weight, a second weight, and a third weight respectively corresponding to the first inference unit, the second inference unit, and the third inference unit, inference results in the performing inference concerning the diagnosis using the data collected under the first condition, the performing inference concerning the diagnosis using the data collected under the first condition and the data collected under the second condition, and the performing inference concerning the diagnosis using the data collected under the second condition.

18. A non-transitory computer-readable storage medium storing a computer program for causing a computer to execute a control method for a diagnosis support apparatus, wherein the computer functions as a first inference unit, a second inference unit, and a third inference unit, the method comprising:

causing the first inference unit to perform inference concerning a diagnosis using data collected under a first condition;

causing the second inference unit to perform inference concerning the diagnosis using the data collected under the first condition and data collected under a second condition different from the first condition;

causing the third inference unit to perform inference concerning the diagnosis using the data collected under the second condition; and integrating, using a first weight, a second weight, and a third weight respectively corresponding to the first inference unit, the second inference unit, and the third inference unit, inference results in the performing inference concerning the diagnosis using the data collected under the first condition, the performing inference concerning the diagnosis using the data collected under the first condition and the data collected under the second condition, and the performing inference concerning the diagnosis using the data collected under the second condition.

* * * * *